United States Patent [19]

Sun

[11] Patent Number: 4,504,579

[45] Date of Patent: Mar. 12, 1985

[54] STABILIZED PEROXIDASE COMPOSITIONS

[75] Inventor: Ming Sun, Mundelein, Ill.

[73] Assignee: Abbott Laboratories, North Chicago, Ill.

[21] Appl. No.: 440,130

[22] Filed: Nov. 8, 1982

[51] Int. Cl.³ .......................... C12Q 1/28; C12N 9/96
[52] U.S. Cl. ....................................... 435/28; 435/188
[58] Field of Search ......................... 435/28, 188, 192

[56] References Cited

U.S. PATENT DOCUMENTS 4,220,722  9/1980  Rowley et al. ..................... 435/188

OTHER PUBLICATIONS

Berkowitz et al., Chemical Abstracts, vol. 96, No. 3, 16803g, (Jan. 18, 1982).

*Primary Examiner*—Lionel M. Shapiro
*Attorney, Agent, or Firm*—James L. Wilcox

[57] ABSTRACT

Novel stable peroxidase compositions are disclosed which are useful as reagents in enzyme immunoassay procedures. In particular the novel peroxidase compositions contain a stabilizer selected from the group consisting of gentamicin, amikacin and tobramycin.

5 Claims, No Drawings

STABILIZED PEROXIDASE COMPOSITIONS

BACKGROUND OF THE INVENTION

Peroxidases and peroxidase conjugates, that is, peroxidases coupled to an immunological component, are relatively unstable, particularly at low concentrations. As a result, compositions containing peroxidases and/or peroxidase conjugates without a suitable stabilizer to inhibit the enzyme inactivation process, exhibit poor shelflife properties, thereby decreasing their commercial applicability.

Peroxidases are enzymes which catalyze the oxidation of certain compounds such as for example, o-phenylene diamine, during which oxidation, a peroxide, in particular hydrogen peroxide, functions as an "acceptor" for a proton donor molecule. Peroxidases may be obtained from plants, for example, horseradish peroxidase (HPO); from vertebrate animals, for example, lactoperoxidase; and from microorganisms such as cytochrome peroxidase from Pseudomonas.

Peroxidases are used for a variety of purposes, in particular, as detectable markers in immunological assay techniques for the detection and determination of immunocomponents, such as haptens, antigens or antibodies. The use of peroxidase labeled immunoreactants is of particular value because the activity or presence of the peroxidase enzyme may be detected visually and the level of activity may be discerned by colorimetric means.

Immunoassay kits useful in performing enzyme immunoassays usually contain as an essential constituent a certain amount of an immunocomponent coupled to a peroxidase. Since such kits will be subject of shipping and storing for variable lengths of time before use, it is essential that the activity of the peroxidase conjugate be maintained as long as possible.

Enzyme conjugates and in particular peroxidase conjugates, are generally stored in an immunological reaction medium containing serum protein, such as for example, fetal calf serum. It has been noted that serum protein contributes to the stability of the conjugate as compared to the stability of the conjugate alone. It is theorized that the serum matrix contributes to maintaining the special structure of the enzyme. However, it has also been observed that the serum protein contributes to the inactivation of the enzyme by extracting detachable hemin moieties from the enzyme structure. This denaturation of peroxidase appears to be due to hemin interactions between the peroxidase and hemin binding proteins from the calf serum. In order to deminish the attraction and thereby the interaction between hemin and serum proteins, various compounds have been proposed as stabilizers for peroxidase compositions. Dawson, et al, in U.S. Pat. No. 4,169,012, describes the use of polyvalent metal ions as stabilizers for peroxidase compositions. Shaffar, in U.S. Pat. No. 4,252,896, discloses the use of 8-anilino-1-naphthalene sulfonic acid (ANS) as a stabilizer for peroxidase compositions.

It is an object of the present invention to provide a novel stable peroxidase composition wherein the peroxidase activity of the composition is maintained for a substantial period of time.

SUMMARY OF THE INVENTION

It has been found that the addition of an effective amount of a stabilizer selected from the group consisting of gentamicin, amikacin and tobramycin, to a composition containing a peroxidase and/or peroxidase conjugate, substantially increases the stability of the composition.

DETAILED DESCRIPTION OF THE INVENTION

The stabilizers useful in the compositions of the present invention are selected from the group consisting of gentamicin, amikacin and tobramycin. It has been found that such compounds stabilize peroxidase and/or peroxidase conjugates by substantially inhibiting the peroxidase inactivation process and thereby maintain the structural integrity of the enzyme or enzyme conjugate. It is preferred to employ gentamicin as the stabilizer in the compositions of the present invention.

The term "peroxidase conjugate" refers to an immunocomponent, such as a hapten, antigen, antibody, or a protein binding substance such as avidin or biotin, coupled to peroxidase. Such conjugates are either commercially available or readily prepared by one of ordinary skill in the art employing conventional techniques. The specific hapten, antigen, antibody or protein binding substance employed is readily ascertained by one of ordinary skill in the art depending on the specific immunoassay being conducted.

An "effective amount of a stabilizer" refers to the concentration of stabilizer required to provide a substantial inhibition of peroxidase inactivation in a peroxidase or peroxidase conjugate composition when compared to compositions not containing a stabilizer. Such concentrations are readily ascertained by one of ordinary skill in the art. It has been found that minimum concentration of stabilizers in the compositions of the present invention necessary for obtaining a stabilizing effect is about 0.005% (weight/volume). Although there is no critical maximum concentration of stabilizer in the compositions of the present invention, amounts greater than 1.0% (weight/volume) concentration are acceptable but unnecessary and costly. It is preferred to employ a stabilizer in the composition of the present invention of approximately 0.1% (weight/volume).

The stabilizers of the present invention are generally present in the compositions of the present invention in an ionic form. It is preferred to add salts of gentamicin, amikacin or tobramycin, such as sulfates, phosphates, halides or nitrates, to the peroxidase or peroxidase conjugates.

In addition to peroxidase and/or peroxidase conjugates and stabilizers, other constituents may be added to the compositions of the present invention. In particular, the compositions of the present invention may include, but not limited to, serum proteins, such as fetal calf serum, rabbit serum, pig serum and the like and buffers, such as tris·HCl buffer, phosphate buffered saline and the like.

Although the stable peroxidase compositions are preferable aqueous compositions, the peroxidase compositions may be marketed as a lyophilized product.

The following example serves to further illustrate the present invention.

EXAMPLE 1

A 1:1 mixture of commercially available normal rabbit serum and normal pig serum was pooled. The serum was filtered to remove any precipitates and the filtrate was diluted with an equal volume of 0.1 M tris buffer (pH 8.6) to provide a final concentration of 50% serum.

20 ml aliquots of the serum composition was poured into three individual vials. To one vial (Sample A) was added 20 mg of gentamicin sulfate and to a second vial (Sample B) was added 20 mg of sodium azide. The third vial (Sample C) was maintained as a control. Then, 0.08 ml of an avidin-horseradish peroxidase conjugate stock solution was added to each vial resulting in a final enzyme conjugate concentration of between 5 to 10 μg/ml in each vial. The resulting mixtures were stirred for one hour at room temperature. A 5 ml aliquot of each solution was placed in a plastic vial and stored at 45° C. for 24 hours. In addition, a control sample (Sample D) was maintained at 4° C.

The peroxidase activity of Samples A–D was determined in accordance with the following procedure:

(1) A 50 μl aliquot of a standard containing 2500 μIU/ml prolactin and a 50 μl aliquot of a blank were added to appropriate wells of a reaction tray.

(2) To each well containing the standard or blank was added 200 μl of biotin labeled anti-human prolactin antibody.

(3) A polystyrene bead coated with antibody specific to prolactin was added to each well and the reaction trays were covered and shaken at room temperature for 2 hours.

(4) A 50 μl aliquot of Sample A was added to each well and the reaction trays were covered and shaken for thirty minutes.

(5) The beads were washed and excess liquid was completely removed.

(6) The beads from the wells originally containing the samples and controls were transferred to assay tubes to which was then added 300 μl of a freshly prepared substrate solution containing approximately 27 mg of σ-phenylene diamine·2HCl in 5 ml of citrate-phosphate buffer containing 0.02% hydrogen peroxide at a pH of 5.5. The tubes were then incubated for 30 minutes at room temperature.

(7) Following the incubation, 1 ml of 1N sulfuric acid was added to each tube and the absorbance of the resulting sample and control solutions were read on a spectrophotometer at 492 nm.

The peroxidase activity of Sample A was calculated as the difference between the absorbance of the 2500 μIU/ml standard and the blank. The peroxidase activity of Samples B–D were also determined utilizing the above procedure.

Table I illustrates the peroxidase activities of Samples A–D obtained utilizing the above procedure.

ΔA refers to the absorbance difference between the 2500 μIU/ml standard and the blank and % Activity is the peroxidase activity of the Sample with respect to Sample A (100%).

TABLE I

|  | ΔA | % Activity |
|---|---|---|
| Sample A | 1.400 | 100 |
| Sample B | 0.495 | 35 |
| Sample C | 1.120 | 80 |
| Sample D | 1.298 | 93 |

Although this invention has been described with respect to specific modification, the details thereof are not to be construed as limitations, for it will be apparent that various equivalents, changes and modification may be resorted to without departing from the spirit and scope thereof and it is understood that such equivalent embodiments are intended to be included therein.

What is claimed is:

1. A reagent composition for use in enzyme immunoassay techniques comprising a peroxidase conjugate and an effective amount of a stabilizer selected from the group consisting of gentamicin, amikacin and tobramycin.

2. A reagent composition according to claim 1 wherein the stabilizer is gentamicin.

3. A reagent composition according to claim 2 wherein the stabilizer is a horseradish peroxidase conjugate.

4. A reagent composition as in any of claims 1–3 wherein the stabilizer is present in a concentration greater than 0.005% (weight/volume).

5. A reagent composition as in any of claims 1–3 wherein the stabilizing concentration is approximately 0.1% (weight/volume).

* * * * *